(12) United States Patent
Ho et al.

(10) Patent No.: US 10,704,890 B2
(45) Date of Patent: Jul. 7, 2020

(54) DYNAMIC MOTION DETECTION SYSTEM

(71) Applicant: Giant Manufacturing Co., Ltd., Taichung (TW)

(72) Inventors: Wei-Chieh Ho, Taichung (TW); Chien-Hung Chen, Miaoli County (TW); Ji-De Huang, Hsinchu (TW); Jui-Yen Chang, Taoyuan (TW); Yu-Fu Mao, Hsinchu (TW)

(73) Assignee: Giant Manufacturing Co., Ltd., Taichung (TW)

( * ) Notice: Subject to any disclaimer, the term of this patent is extended or adjusted under 35 U.S.C. 154(b) by 607 days.

(21) Appl. No.: 15/439,952

(22) Filed: Feb. 23, 2017

(65) Prior Publication Data

US 2018/0045502 A1    Feb. 15, 2018

(30) Foreign Application Priority Data

Aug. 10, 2016  (TW) .............................. 105125440 A

(51) Int. Cl.
*G01B 11/00*    (2006.01)
*G06K 9/00*    (2006.01)
(Continued)

(52) U.S. Cl.
CPC .......... *G01B 11/002* (2013.01); *A61B 5/1127* (2013.01); *B62J 99/00* (2013.01);
(Continued)

(58) Field of Classification Search
CPC ................................................ G01B 11/002
See application file for complete search history.

(56) References Cited

U.S. PATENT DOCUMENTS 5,828,770 A * 10/1998 Leis .................. G01S 5/163
  382/103
6,061,644 A *  5/2000 Leis .................. G01S 5/163
  382/103

(Continued)

FOREIGN PATENT DOCUMENTS

JP    2000258123    9/2000
JP    2002505412    2/2002
(Continued)

OTHER PUBLICATIONS

"Office Action of Taiwan Counterpart Application," dated Jun. 13, 2017, p. 1-p. 11, in which the listed references were cited.
(Continued)

*Primary Examiner* — Raymond L Nimox
(74) *Attorney, Agent, or Firm* — JCIPRNET

(57) ABSTRACT

A dynamic motion detection system including a plurality of active independent emitting elements, a signal capturing apparatus, and a computing apparatus is provided. The active independent emitting elements are suitable for being respectively affixed to different parts of a person to-be-tested and actively emitting positioning signals having preset wavelengths. The signal capturing apparatus is configured to capture the positioning signal of each of the active independent emitting elements and calculate a plurality of emitting coordinates according to the positioning signals. The computing apparatus is configured to control operation of the signal capturing apparatus and receive the emitting coordinates from the signal capturing apparatus. The computing apparatus defines a corresponding relationship between the emitting coordinates and the active independent emitting elements by comparing a geometry relationship among the emitting coordinates.

20 Claims, 6 Drawing Sheets

(51) Int. Cl.
*A61B 5/11* (2006.01)
*B62J 99/00* (2020.01)
*G01P 13/00* (2006.01)
*G09B 19/00* (2006.01)
*G06K 9/32* (2006.01)

(52) U.S. Cl.
CPC .......... *G01P 13/00* (2013.01); *G06K 9/00342* (2013.01); *G09B 19/00* (2013.01); *A61B 2503/10* (2013.01); *B62J 2099/004* (2013.01); *B62J 2099/0013* (2013.01); *G06K 2209/3225* (2013.01); *G06K 2209/401* (2013.01)

(56) References Cited

U.S. PATENT DOCUMENTS

| | | | | |
|---|---|---|---|---|
| 6,324,296 | B1* | 11/2001 | McSheery | G06T 7/80 |
| | | | | 250/203.3 |
| 9,360,932 | B1* | 6/2016 | Lukashevich | G06F 3/011 |
| 9,886,624 | B1* | 2/2018 | Marty | G06T 7/20 |
| 2003/0077556 | A1* | 4/2003 | French | A61B 5/1113 |
| | | | | 434/258 |
| 2007/0142177 | A1* | 6/2007 | Simms | A61B 5/1127 |
| | | | | 482/8 |
| 2010/0076721 | A1 | 3/2010 | Simms et al. | |
| 2010/0321246 | A1* | 12/2010 | Troesken | G01S 13/878 |
| | | | | 342/463 |
| 2011/0060537 | A1* | 3/2011 | Moodie | A61B 5/1036 |
| | | | | 702/41 |
| 2013/0120445 | A1* | 5/2013 | Shimomura | G06F 3/017 |
| | | | | 345/629 |
| 2014/0243686 | A1* | 8/2014 | Kimmel | A61B 5/1114 |
| | | | | 600/476 |
| 2014/0379135 | A1 | 12/2014 | Kristiansen et al. | |
| 2015/0051718 | A1* | 2/2015 | Inoue | A61B 5/1127 |
| | | | | 700/91 |
| 2016/0235344 | A1* | 8/2016 | Auerbach | A61B 5/087 |

FOREIGN PATENT DOCUMENTS

| | | |
|---|---|---|
| JP | 2012120648 | 6/2012 |
| TW | 201337639 | 9/2013 |
| TW | 201515635 | 5/2015 |
| WO | 9930182 | 6/1999 |
| WO | 2015058154 | 4/2015 |

OTHER PUBLICATIONS

"Office Action of Japan Counterpart Application", dated Apr. 19, 2018, p. 1-p. 5.

"Office Action of Taiwan Counterpart Application," dated Jan. 15, 2018, p. 1-p. 12, in which the listed references were cited.

Ferrigno et al., "Procedure to automatically classify markers in biomechanical analysis of whole-body movement in different sports activities", Medical & Biological Engineering & Computing, May 1988, pp. 321-324.

"Search Report of Europe Counterpart Application", dated Nov. 7, 2017, p. 1-p. 8, in which the listed references were cited.

* cited by examiner

DYNAMIC MOTION DETECTION SYSTEM

CROSS-REFERENCE TO RELATED APPLICATION

This application claims the priority benefit of Taiwan application serial no. 105125440, filed on Aug. 10, 2016. The entirety of the above-mentioned patent application is hereby incorporated by reference herein and made a part of this specification.

BACKGROUND

Field of the Invention

The invention is directed to a motion detection technique and more particularly, to a dynamic motion detection system.

Description of Related Art

A so-called bike fitting technique has been recently developed for athletes to achieve the ultimate achievement with their physical fitness in cope with the bicycle operations in bicycle races. Through the bike fitting technique, adjustable modules of a bicycle can be adjusted to suit an optimal riding posture according to the body shape and motions of an athlete. The bike fitting technique was only applied to the bicycle race in the early stage. Nevertheless, as bicycle riding becomes increasingly popular, more and more consumers treat bicycle riding as a sport in leisure time, and their demands for bike fitting have also been increased. The consumers now can also pay for experiencing the bike fitting service.

The conventional bike fitting technique serves bike fitting for the consumers and their bicycles to be fit, such that the adjustable modules of the bicycles can be adjusted in coordination with body shapes and motions of the consumers to achieve an optimal riding posture. However, in the conventional bike fitting service, the body size of a person to-be-tested is statically measured and is regarded as a basis for adjustment. After the adjustment, the person to-be-tested is requested for a riding trial and a fine adjustment is performed based on the riding experience of the person to-be-tested. In this way, it takes a long time for calibration. Additionally, riding habits, physical flexibility and muscle strength vary with persons, such static fitting manner in most cases encounters difficulties in adjusting the bicycle to meet the hardware configuration that is best suitable for the rider.

Some dynamic motion detection systems have been proposed in current applications, in which a dynamic riding status is detected to learn actual riding motions and habits of a person to-be-tested, thereby improving deficiencies of the conventional static fitting technique. However, in a current dynamic motion detection system, the body parts of the person to-be-tested are usually detected by a passive means, e.g., an image recognition operation. However, such detection means is weak in its poor resolution and has difficulty in accurately detecting motions of the person to-be-tested at different time points in a condition that the motions of the person to-be-tested are continuous.

In comparison with the passive detection means, an active dynamic motion detection system can facilitate recognizing the motions of the person to-be-tested at different time points. Specifically, in the conventional active dynamic motion detection system, serial connected emitting elements are affixed to the person to-be-tested and activated one by one according to a preset rule. In this way, signals emitted in turn by the emitting elements are detected by a detector. A processor of the active dynamic motion detection system can compute the signals to recognize the motions of the person to-be-tested. Nevertheless, this method has two disadvantages. First, the method of the emitting elements serially emitting the signals in turn may result in time difference between the signals collected by the system, which easily leads to errors in determination. Second, a wire used for serially connecting each of the emitting elements cause troubles and obstructions to the person to-be-tested during the test.

SUMMARY

The invention provides a dynamic motion detection system capable of resolving the issues encountered by the conventional technique.

A dynamic motion detection system of the invention includes a plurality of active independent emitting elements, a signal capturing apparatus and a computing apparatus. The active independent emitting elements are suitable for being respectively affixed to different parts of a person to-be-tested, and each of the active independent emitting elements is configured to actively emit a positioning signal having a preset wavelength. The signal capturing apparatus is configured to capture the positioning signal of each of the active independent emitting elements and obtain a plurality of emitting coordinates according to the positioning signals. The computing apparatus is configured to control operation of the signal capturing apparatus and receive the emitting coordinates from the signal capturing apparatus. The computing apparatus defines a corresponding relationship between the emitting coordinates and the active independent emitting elements by comparing a geometry relationship among the emitting coordinates.

To sum up, the invention provides a dynamic motion detection system marking the body parts of the person to-be-tested by using the active independent emitting elements. The positioning signal of each marked point is an independently emitted signal and is actively emitted, rather than passively detected. Thus, the system of the invention can contribute to preventing the exercise motions of the person to-be-tested from being affected by the wire and mitigating environment interference, so as to enhance accuracy of detecting the marked points. Moreover, in the invention, the corresponding relationship between the detected emitting coordinates or three-dimensional (3D) coordinates obtained through calculation and the marked points can be determined according to the relative geometry relationship among each of the marked points, and thereby, the exercise motion model of the person to-be-tested can be analyzed and established only by using the information in a signal image frame, so as to improve continuity and accuracy of the detected motions.

Due to the sequence of emitting the serial emitting elements requiring to be preset according to a preset rule, the computing apparatus directly sets a received signal directly to correspond to an emitting element on a specific body part according to the preset rule. However, the motion of each body part of the person to-be-tested is continuous without any pause, but the serial emitting elements needs a period of time to complete the operation of emitting the signals in turn. Therefore, deviation occurs to the dynamic operation detection performed according to the serially emitted signals due to the emitting signals being not detected at the same time. Comparatively, the active independent emitting elements of the invention perform the operation of emitting the positioning signal independently, and thus, the positioning signals corresponding to the body parts can be instantly and simultaneously detected. In this way, through the calculation of the relative relationship among the emitting coordinates, the corresponding relationship between the positioning signal emitted by each of the active independent emitting elements and each of the body parts can be recognized, such that the accuracy of detecting the dynamic motions of the person to-be-tested according to the simultaneously detected positioning signals can be enhanced.

To make the above features and advantages of the invention more comprehensible, embodiments accompanied with drawings are described in detail below.

BRIEF DESCRIPTION OF THE DRAWINGS

The accompanying drawings are included to provide a further understanding of the invention, and are incorporated in and constitute a part of this specification. The drawings illustrate embodiments of the invention and, together with the description, serve to explain the principles of the invention.

DESCRIPTION OF EMBODIMENTS

Figure 1:
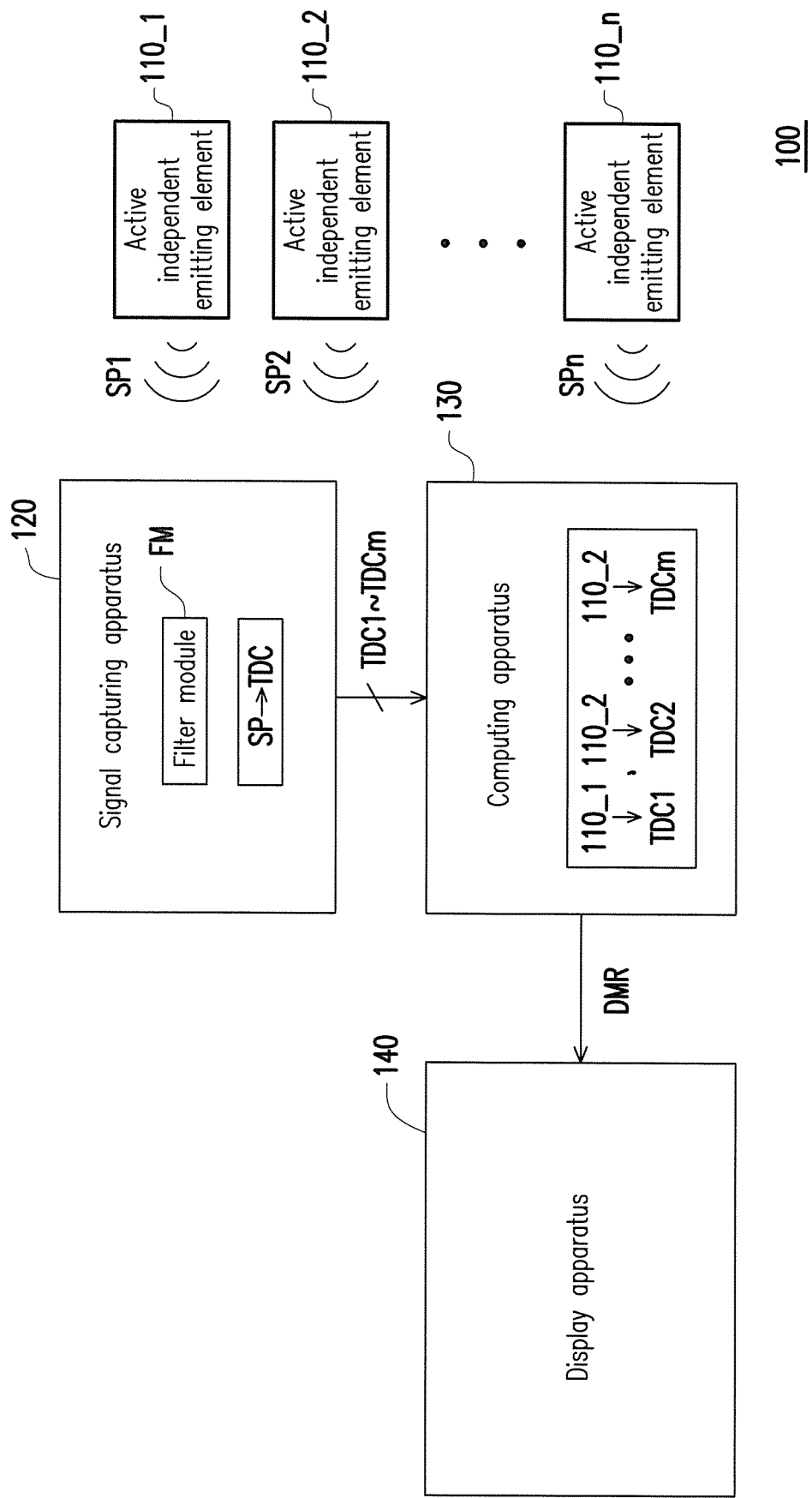
FIG. 1 is a schematic functional block diagram illustrating a dynamic motion detection system according to an embodiment of the invention.

In order to make the content of the invention clearer, the following embodiments are illustrated as examples that can be truly implemented by the invention. In additionally, wherever possible, the same reference numbers are used in the drawings and the description to refer to the same or like parts.

FIG. 1 is a schematic functional block diagram illustrating a dynamic motion detection system according to an embodiment of the invention. A dynamic motion detection system 100 of the present embodiment may be configured to detect a dynamic motion (particularly, a dynamic riding motion) of a person to-be-tested and present detected results in a data or image form, which contributes to adjusting exercise motions for the person to-be-tested, or optimally fitting hardware specification, such as a frame size, bicycle body configuration and so on. Referring to FIG. 1, the dynamic motion detection system 100 of the present embodiment includes a plurality of active independent emitting elements 110_1 to 110_n, a signal capturing apparatus 120, a computing apparatus 130 and a display apparatus 140. The number n is a positive greater than or equal to 2 and may be decided based on a designer's design demand.

In the present embodiment, the active independent emitting elements 110_1 to 110_n are suitable for being respectively affixed to different parts of a person to-be-tested and are controlled to emit positioning signals SP1 to SPn having a preset wavelength. Positions to which the active independent emitting elements 110_1 to 110_n are affixed may be selected according to an exercise type to be detected. For example, if a bicycle riding motion of the person to-be-tested is to be detected, the active independent emitting elements 110_1 to 110_n may be selectively affixed to positions, such as a wrist, a shoulder, an elbow, the waist, a knee, a toe and an ankle of the person to-be-tested, so as to mark several specific parts with greater motions during the exercise.

As for the hardware, in an exemplary embodiment, the active independent emitting elements 110_1 to 110_n may be implemented by active emitting elements capable of emitting visible light. For example, the active independent emitting elements 110_1 to 110_n may be light-emitting diodes (LEDs). In this application, the positioning signals SP1 to SPn may be, for example, lightwave signals with preset wavelengths within a visible wavelength range (about 380 nm to 780 nm).

In another exemplary embodiment, the active independent emitting elements 110_1 to 110_n may be implemented by signal emitting elements capable of emitting invisible light. For example, the active independent emitting elements 110_1 to 110_n may be, for example, infrared (IR) emitters or active radio frequency identification (RFID) tags. In an application that the IR emitters are used as the active independent emitting elements 110_1 to 110_n, the positioning signals SP1 to SPn may be, for example, IR signals with preset wavelengths within an IR wavelength range (about 760 nm to 1000 nm). In an application that the active RFID tags are used as the active independent emitting elements 110_1 to 110_n, the positioning signals SP1 to SPn may be, for example, RF/microwave signals with wavelengths within an RF signal wavelength range (about 1 mm to 1 m).

It should be additionally mentioned herein that although the term "affix" is used to describe the configuration relationship between the active independent emitting elements 110_1 to 110_n and the person to-be-tested, but not limited to an affixing means, and any means for fixing the active independent emitting elements 110_1 to 110_n to the body parts of the person to-be-tested, such as fixing by bandages, or locking the active independent emitting elements to the mechanisms by using specific mechanisms meets the aforementioned configuration aspect of affixing.

The signal capturing apparatus 120 is configured to independently capture the positioning signals SP1 to SPn respectively emitted by the active independent emitting elements 110_1 to 110_n and obtain a plurality of emitting coordinates TDC1 to TDCm according to the positioning signals SP1 to SPn, so as to provide the calculated emitting coordinates to the computing apparatus 130.

Specifically, the signal capturing apparatus 120 is an apparatus capable of positioning where the positioning signals SP1 to SPn are emitted from. For example, the signal capturing apparatus 120 may be implemented by a two-eye image capturing apparatus capable of obtaining depth information of a filmed image by capturing a left-eye image and a right-eye image of the image with parallax therebetween, thereby simulating a 3D image viewed by human eyes. The signal capturing apparatus 120 may include a sensing hardware element capable of sensing positioning signals with preset wavelengths, e.g., a photosensitive element or an IR sensor, but the invention is not limited thereto. Due to the positioning signals SP1 to SPn emitted from the active independent emitting elements 110_1 to 110_n being presented as light spots in the left-eye image and the right-eye image captured by the signal capturing apparatus 120, the signal capturing apparatus 120 executes image processing (i.e., SP→TDC) to convert the positioning signals into two-dimensional (2D) coordinates or 3D coordinates.

In an exemplary embodiment, the signal capturing apparatus 120 may obtain 2D emitting coordinates TDC1 to TDCm respectively according to the light spots (corresponding to the positioning signals SP1 to SPn) on the left-eye image and the right-eye image and provide the emitting coordinates TDC1 to TDCm respectively belonging to the left-eye image and the right-eye image to the computing apparatus 130. In another exemplary embodiment, the signal capturing apparatus 120 may analyze a position of each of the light spots (corresponding to the positioning signals SP1 to SPn) on the left-eye image and the right-eye image to calculate 3D emitting coordinates TDC1 to TDCm respectively of the light spots in a space and provide the 3D emitting coordinates TDC1 to TDCm to the computing apparatus 130.

In actual application, for the signal capturing apparatus 120 to preferably recognize the positions where the positioning signals SP1 to SPn are emitted from, the signal capturing apparatus 120 may selectively include a filter module FM. The filter module FM is configured to filter signals with wavelengths outside the preset wavelength range of the positioning signals SP1 to SPn (i.e., only signals with wavelengths within the preset wavelength range can be allowed to enter), and thereby, the signal capturing apparatus 120 can recognize the positioning signals SP1 to SPn more easily.

The computing apparatus 130 is coupled to the signal capturing apparatus 120 and configured to control the operation of the signal capturing apparatus 120 and receive the emitting coordinates TDC1 to TDCm calculated by the signal capturing apparatus 120. The computing apparatus 130 defines a corresponding relationship between the emitting coordinates TDC1 to TDCm and the active independent emitting elements 110_1 to 110_n by comparing a geometry relationship among the emitting coordinates TDC1 to TDCm.

In an exemplary embodiment, if the emitting coordinates TDC1 to TDCm are 2D coordinates on the left-eye image and the right-eye image, the computing apparatus 130 may compare the geometry relationship among the emitting coordinates TDC1 to TDCm respectively on the left-eye image and the right-eye image, so as to define the corresponding relationship between each of the emitting coordinates TDC1 to TDCm and each of the active independent emitting elements 110_1 to 110_n for the left-eye image and the right-eye image. In another exemplary embodiment, if the emitting coordinates TDC1 to TDCm are 3D coordinates obtained according to the depth information, the computing apparatus 130 may compare the geometry relationship among the 3D emitting coordinates TDC1 to TDCm, so as to define the corresponding relationship between the 3D emitting coordinates TDC1 to TDCm and the active independent emitting elements 110_1 to 110_n.

To be more specific, in many exercise types, e.g., bicycle riding, jogging, specific exercise motions are cyclically reciprocated. In the case of the bicycle riding, grips are held by hands, and pedals are usually pedaled by feet back and forth for reciprocating motions. Thus, by observing exercise motions of the person to-be-tested from a specific angle, it can be found that body parts of the person to-be-tested usually move within specific zones, and displacement between each body part has a specific corresponding relationship, which is referred to the geometry relationship in the invention. Specific description and examples related to the details of defining the corresponding relationship between the emitting coordinates TDC1 to TDCm and the active independent emitting elements 110_1 to 110_n by comparing the geometry relationship among the emitting coordinates TDC1 to TDCm will be provided in the embodiments below.

The positions to which each of the active independent emitting elements 110_1 to 110_n is affixed to may be pre-recorded in the computing apparatus 130. Thus, after the corresponding relationship between each of the emitting coordinates TDC1 to TDCm and each of the active independent emitting elements 110_1 to 110_n is determined, the computing apparatus 130 may construct an exercise motion model of the person to-be-tested according to the corresponding relationship and analyze the change of the emitting coordinates TDC1 to TDCm corresponding to the active independent emitting elements 110_1 to 110_n during a detection period, so as to generate a dynamic motion detection result DMR.

Therein, the dynamic motion detection result DMR may be presented on the display apparatus 140 in a data or graphical form. Taking the bike fitting technique for example, the dynamic motion detection result DMR may include, for example, riding motion tacks, a moving speed and a moving acceleration of each of the marked points (i.e., the affixing positions/3D coordinate corresponding to each of the active independent emitting elements 120_1 to 120_n), riding motions in different times, comparison of the riding motions in different times, a maximum extended position during riding, horizontal positions of the pedals, continuous angles of the knee, an angle of the ankle, and so on, which are not limited in the invention.

Besides, in actual application, a human-machine interface may be further provided in the computing apparatus 130, such that an operator may operate the human-machine interface to control the computing apparatus 130 and the display apparatus 140 for functions, such as instantly image displaying, instant analyzing, dynamic playback, record comparison, and so on, during the detection period. Additionally, the instant analyzing function may be available for not only observing an instant length, an angle (including a maximum value, a minimum value and an average value) between the marked points and storing various information during riding for subsequent analysis, but also comparing a substantial relative relation between the marked points with a substantial relative relation between joints of the person to-be-tested, and thereby, a tester may optimize the position of each marked point.

Accordingly, in comparison with the conventional dynamic motion detection system, first, due to the positioning signals SP1 to SPn being actively emitted by the active independent emitting elements 110_1 to 110_n in the invention, the signal capturing apparatus 120 can detect the positions of the marked points more accurately, without being affected by the environment. Additionally, the dynamic motion detection system 100 of the invention may use signals with invisible wavelengths as the signals for detection, thereby avoiding detection interference which may be caused by an ambient light source.

Then, the active independent emitting elements 110_1 to 110_n of the invention emits the positioning signals SP1 to SPn independently, thereby preventing the exercise motions of the person to-be-tested being interfered by the wire.

Moreover, in the invention, the corresponding relationship between the detected emitting coordinates TDC1 to TDCm and the active independent emitting elements 110_1 to 110_n are defined through comparing the relative geometry relationship among the emitting coordinates TDC1 to TDCm, and thus, the invention can analyze the exercise motion model of the person to-be-tested and obtain an accurate result by using the information of only one image frame, without analyzing changes of a plurality of image frames. Additionally, the corresponding relationship between the emitting elements and the detected emitting coordinates is not defined by serially enabling the emitting elements in the invention, and thus, the issue of incapability of instantly and synchronously presenting the dynamic status of each marked point in serial detection can be avoided.

Figure 2:
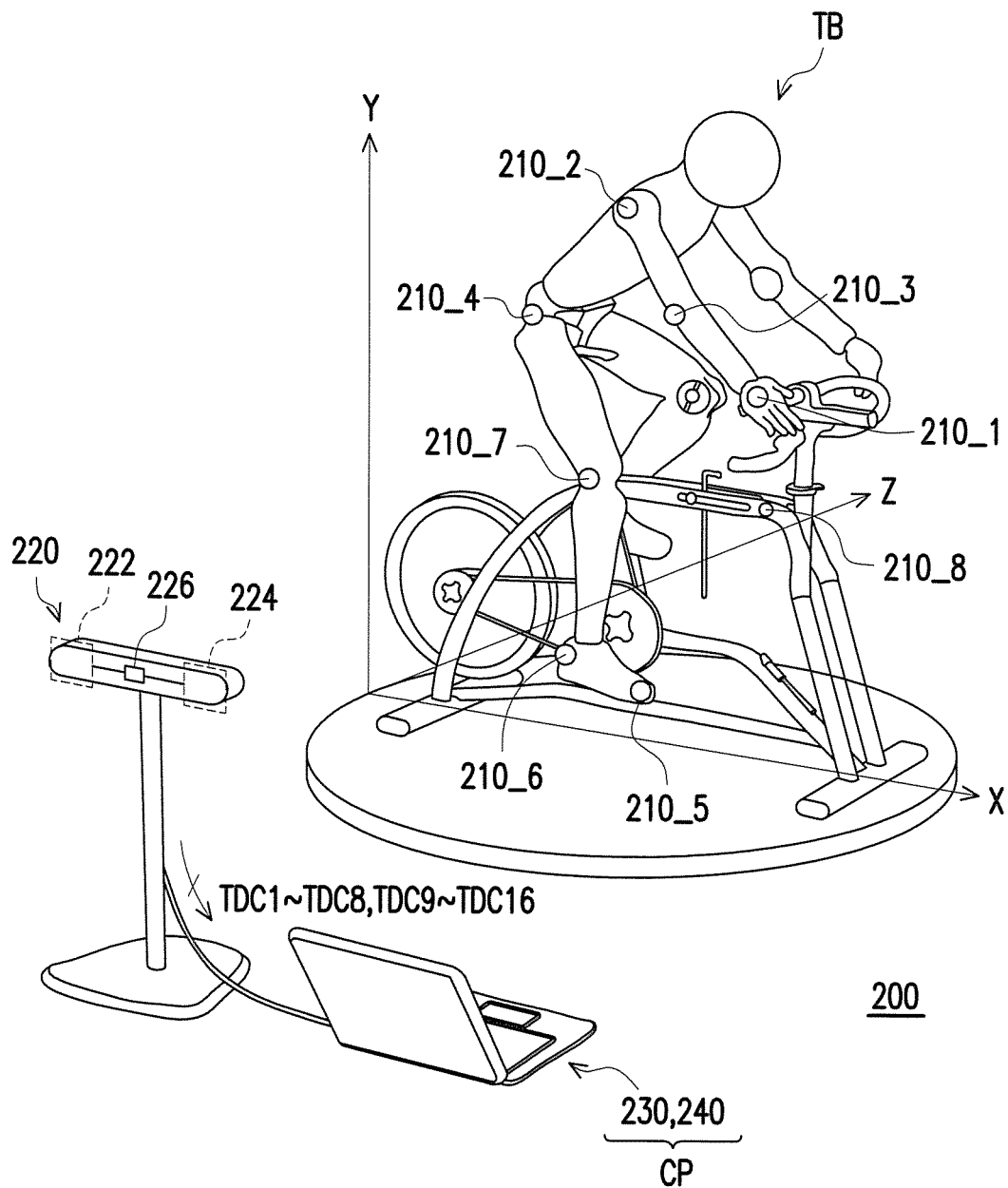
FIG. 2 is a schematic structural diagram illustrating a dynamic motion detection system according to an embodiment of the invention.

FIG. 2 is illustrated for describing an exemplary specific structure of the dynamic motion detection system of the invention. FIG. 2 is a schematic structural diagram illustrating a dynamic motion detection system according to an embodiment of the invention.

Referring to FIG. 2, a dynamic motion detection system of the present embodiment uses a dynamic riding motion detection system 200 for detecting a bicycle riding motion of a person to-be-tested TB for example. The dynamic riding motion detection system 200 includes active independent emitting elements 210_1 to 210_8, a signal capturing apparatus 220, a computing apparatus 230 and a display apparatus 240. The active independent emitting elements 210_1 to 210_8 of the present embodiment are implemented by IR emitters (which are referred to as IR emitters 210_1 to 210_8 below), for example, the signal capturing apparatus 220 is implemented by a two-eye image capturing apparatus (which is referred to as a two-eye image capturing apparatus 220), for example, and the computing apparatus 230 together with the display apparatus 240 is implemented by a computer (which is referred to as a computer CP below) including a processing unit and a display, but the invention is not limited thereto.

In the present embodiment, the IR emitters 210_1 to 210_7 are respectively affixed to a wrist, a shoulder, an elbow, a waist, a toe, an ankle and a knee of the person to-be-tested TB, for example, such that the parts serve as marked points for detecting exercise motions, but the invention is not limited thereto.

The two-eye image capturing apparatus 220 includes two image capturing modules 222 and 224 and an image processing module 226. The two image capturing modules 222 and 224 are disposed with a predetermined interval from each other, thereby respectively capturing a left-eye image and a right-eye image. The image processing module 226 is coupled to the image capturing modules 222 and 224 and configured to perform image processing and analysis on the left-eye image and the right-eye image. For example, the image processing module 226 may establish 3D image information according to the left-eye image and the right-eye image captured by the image capturing modules 222 and 224 and may also perform an image fine tuning process respectively on the left-eye image and the right-eye image. Alternatively, the image processing module 226 may perform image displacement correction on the left-eye image and the right-eye image to avoid a detection error caused by the displacement of the image capturing modules 222 and 224.

It should be mentioned that FIG. 2 illustrates that the image processing module 226 transmits emitting coordinates TDC1 to TDC8 corresponding to the marked points on the left-eye image and emitting coordinates TDC9 to TDC16 corresponding to the marked points on the right-eye image to the computer CP, for example, but the invention is not limited thereto. In another embodiment, the image processing module 226 may also first establish the 3D image information according to the left-eye image and the right-eye image, and then, calculate the emitting coordinate corresponding to each marked point in an XYZ space according to the 3D image information.

It is to be additionally mentioned that in the present embodiment, a filter module (not shown) may be, for example, an IR filter attached to lens of the image capturing modules 222 and 224, thereby limiting the image capturing modules 222 and 224 to receive only light signals with wavelengths within a IR wavelength rang, such that the image processing module 226 performs image processing to recognize the positions of the marked points in a faster speed.

The computer CP receives the emitting coordinates TDC1 to TDC16 from the two-eye image capturing apparatus 220 and defines a corresponding relationship between each of the emitting coordinates TDC1 to TDC16 and each of the IR emitters 210_1 to 210_8 affixed to different positions according to a relative geometry relationship among the received emitting coordinates TDC1 to TDC16. In the present embodiment, the IR emitter 210_1 is fixed to the wrist of the person to-be-tested, the IR emitter 210_2 is fixed to the shoulder of the person to-be-tested; IR emitter 210_3 is fixed to the elbow of the person to-be-tested, the IR emitter 210_4 is fixed to the buttock of the person to-be-tested; the IR emitter 210_5 is fixed to the toe of the person to-be-tested; the IR emitter 210_6 is fixed to the ankle of the person to-be-tested; the IR emitter 210_7 is fixed to the knee of the person to-be-tested; and the IR emitter 210_8 is fixed to a predetermined position on the bicycle. However, the number and the positions of affixing the IR emitters may be determined based on actual application, and are not limited in the invention.

Figure 3:
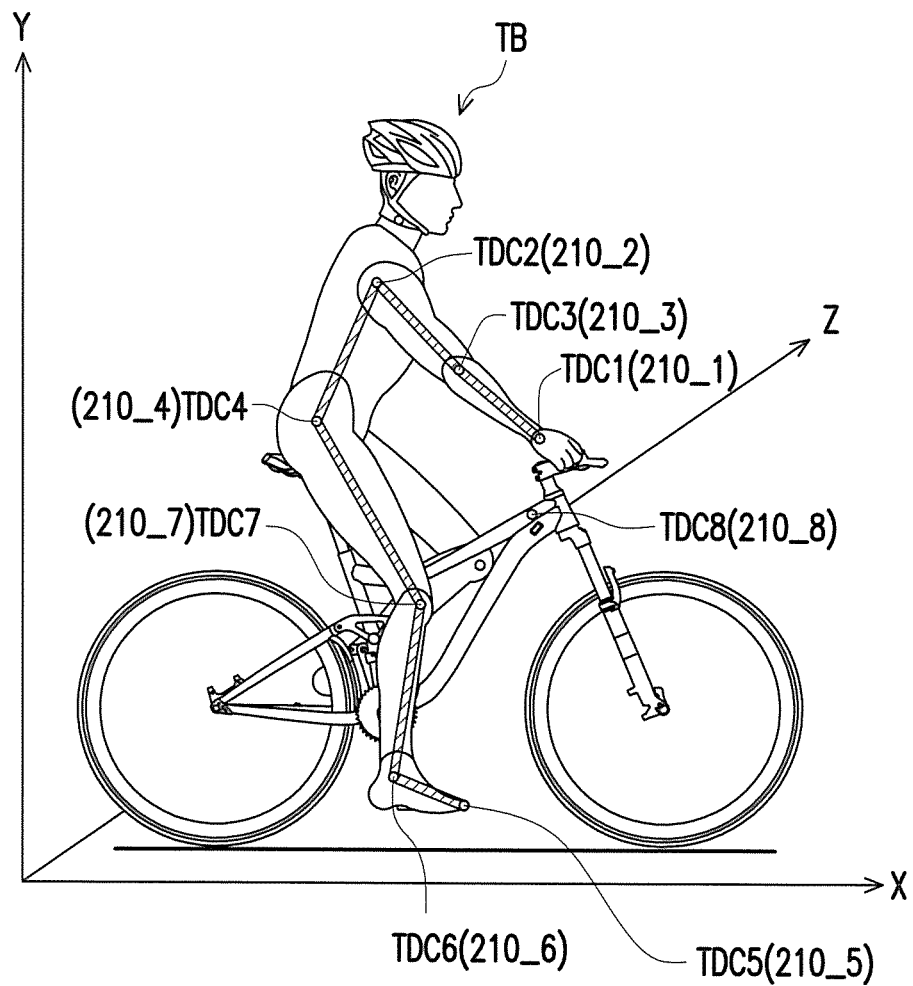
FIG. 3 is a schematic diagram illustrating dynamic detection of a riding motion according to an embodiment of the invention.

FIG. 3 is further illustrated for description. In the system structure of the present embodiment, the left emitting coordinates TDC1 to TDC8 obtained by the computer CP within a left-eye image are as illustrated in FIG. 3. However, even though FIG. 3 illustrates only the left-eye image for description, a person ordinarily skilled in the art may derive that the right-eye image of the invention may be processed in the same way according to the description related to FIG. 3.

Referring to FIG. 2 together with FIG. 3, for descriptive convenience, the left emitting coordinates TDC1 to TDC8 and the IR emitters 210_1 to 210_8 are respectively given with corresponding reference numerals; however, when the computer CP obtains the left emitting coordinates TDC1 to TDC8 in the beginning, the computer CP cannot be sure of the corresponding relationship between each of the left emitting coordinates TDC1 to TDC8 and each of the IR emitters 210_1 to 210_8. In other words, as the left emitting coordinates TDC1 to TDC8 are initially received, and the corresponding relationship between the each of the left emitting coordinates TDC1 to TDC8 and the IR emitters 210_1 to 210_8 are not yet defined, the computer CP is incapable of determining whether the left emitting coordinates TDC1 to TDC8 are respectively coordinates corresponding to different parts of the person to-be-tested TB or coordinates corresponding to the IR emitters 210_1 to 210_8 on the bicycle body. For instance, before defining the corresponding relationship between each of the left emitting coordinates TDC1 to TDC8 and the IR emitters 210_1 to 210_8, the computer CP is incapable of confirming that the left emitting coordinate TDC1 is corresponding to the IR emitter 210_1 on the wrist.

Thus, after receiving the left emitting coordinates TDC1 to TDC8, the computer CP first calculates a relative distance between each two of the left emitting coordinates TDC1 to TDC8 and absolute coordinate values in the vertical coordinate system. In a normal riding motion, the shoulder is located at the highest position, and thus, the computer CP compares the coordinate values of the left emitting coordinates TDC1 to TDC7 along a first axial direction (i.e., the Y-axial direction illustrates in FIG. 3), thereby obtaining the left emitting coordinate TDC2 having the maximum coordinate value along the Y-axial direction to serve it as the coordinate corresponding to the IR emitter 210_2 affixed to the shoulder.

Similarly, the wrist is usually located at the forwardmost position in the normal riding motion, and thus, the computer CP may compare the coordinate values of the left emitting coordinates TDC1 to TDC7 along a second axial direction (i.e., the X-axial direction illustrated in FIG. 3), thereby obtaining the left emitting coordinate TDC1 having the maximum coordinate value along the X-axial direction to serve it as the coordinate corresponding to the IR emitter 210_1 affixed to the wrist.

In an embodiment, the computer CP may define the left emitting coordinate TDC8 which does not displace along with time as a coordinate corresponding to the IR emitter 201_8 affixed to a reference point. Additionally, in an embodiment, the IR emitter 201_8 affixed to the bicycle body is predetermined to serve as the reference point, and thus, after defining the left emitting coordinate TDC1 as the coordinate corresponding to the IR emitter 210_1 affixed to the wrist, the computer CP may further define the left emitting coordinate TDC8 closest to the left emitting coordinate TDC1 as the coordinate corresponding to the IR emitter 201_8 affixed to the predetermined position on the bicycle. Alternatively, in an embodiment, the computer CP may directly define the left emitting coordinate TDC8 conforming to a preset coordinate as the coordinate corresponding to the IR emitter 201_8 affixed to the predetermined position on the bicycle.

In an embodiment, after defining the corresponding relationship between the left emitting coordinates TDC1 and TDC2, by comparing the undefined left emitting coordinates TDC3 to TDC7, the computer CP may define the left emitting coordinate TDC3 located between the coordinate corresponding to the IR emitter 210_2 (i.e., the left emitting coordinate TDC2) and the coordinate corresponding to the IR emitter 210_1 (i.e., the left emitting coordinate TDC1) as the coordinate corresponding to the IR emitter 210_3 affixed to the elbow. In an embodiment, the computer CP may compare which one among the undefined left emitting coordinates TDC3 to TDC7 is closest to the left emitting coordinate TDC1 corresponding to the IR emitter 210_1 on the wrist and define the left emitting coordinate TDC3 located at a position closest to the wrist as the coordinate corresponding to the IR emitter 210_3 affixed to the elbow.

Figure 4:
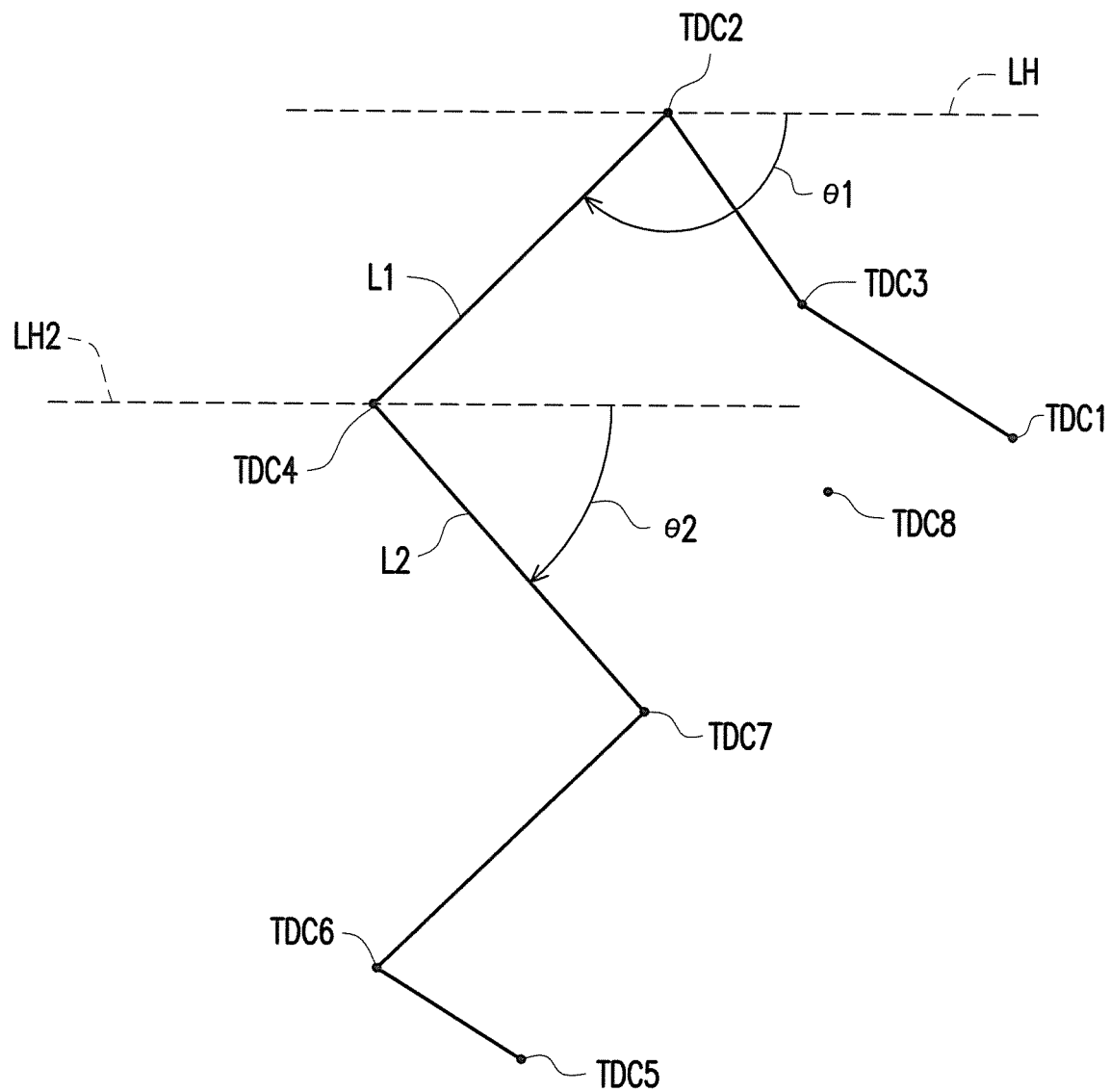
FIG. 4 is a schematic diagram illustrating the left emitting coordinates according to an embodiment of the invention.

Then, in an embodiment, the computer CP may define the left emitting coordinate TDC4 having the minimum coordinate value along the second axial direction (i.e., the X-axial direction illustrated in FIG. 3) as the coordinate corresponding to the IR emitter 210_4 affixed to the buttock. Additionally, in another embodiment, the computer CP may respectively connect the undefined left emitting coordinates TDC4 to TDC7 and the coordinate corresponding to the IR emitter 210_2 (i.e., the left emitting coordinate TDC2) to obtain a plurality of first connections respectively corresponding to the left emitting coordinates TDC4 to TDC7. The computer CP may respectively calculate a plurality of first included angles between the first connections and a horizontal line passing through the coordinate corresponding to the IR emitter 210_2. The computer CP may define the left emitting coordinate TDC4 corresponding to the maximum first included angle among the undefined left emitting coordinates TDC4 to TDC7 as the coordinate corresponding to the IR emitter 210_4 affixed to the buttock. Referring to FIG. 4, FIG. 4 is a schematic diagram illustrating the left emitting coordinates according to an embodiment of the invention. A first included angle $\theta 1$ between the first connection L1 corresponding to the left emitting coordinate TDC4 and a horizontal line LH1 has the maximum value in comparison with other first included angles (not shown) corresponding to the left emitting coordinates TDC5 to TDC7, and thus, the computer CP may define the left emitting coordinate TDC4 as the coordinate corresponding to the IR emitter 210_4.

Afterwards, similarly, in an embodiment, the computer CP may respectively connect the undefined left emitting coordinates TDC5 to TDC7 with the coordinate corresponding to the IR emitter 210_4 (i.e., the left emitting coordinate TDC4) to obtain a plurality of second connections respectively corresponding to the left emitting coordinates TDC5 to TDC7. The computer CP may respectively calculate a plurality of second included angles between the second connections and a horizontal line passing through the coordinate corresponding to the IR emitter 210_4. The computer CP may define the left emitting coordinate TDC7 corresponding to the minimum second included angle among the undefined left emitting coordinates TDC5 to TDC7 as the coordinate corresponding to the IR emitter 210_7 affixed to the knee. As illustrated in FIG. 4, a second included angle $\theta 2$ between a second connection L2 corresponding to the left emitting coordinate TDC7 and a horizontal line LH2 has the minimum value in comparison with other second included angles (not shown) corresponding to the left emitting coordinates TDC5 to TDC6, and thus, the computer CP may define the left emitting coordinate TDC7 as the coordinate corresponding to the IR emitter 210_7 affixed to the knee.

Similarly, since a toe is usually located the lowest position in the riding motion, the computer CP may compare the coordinate values of the undefined left emitting coordinates TDC5 to TDC7 along the Y-axial direction, thereby obtaining the left emitting coordinate TDC5 having the minimum coordinate value along the Y-axial direction to define it as the coordinate corresponding to the IR emitter 210_5. Then, in an embodiment, the computer CP may define the left emitting coordinate TDC6 closest to the coordinate corresponding to the IR emitter 210_5 as the coordinate corresponding to the IR emitter 210_6 affixed to the ankle. Alternatively, in an embodiment, after defining the corresponding relationship for the left emitting coordinates TDC1 to TDC5 and TDC7, the computer CP may define the undefined left emitting coordinate TDC6 as the coordinate corresponding to the IR emitter 210_6 affixed to the ankle.

Figure 5A:
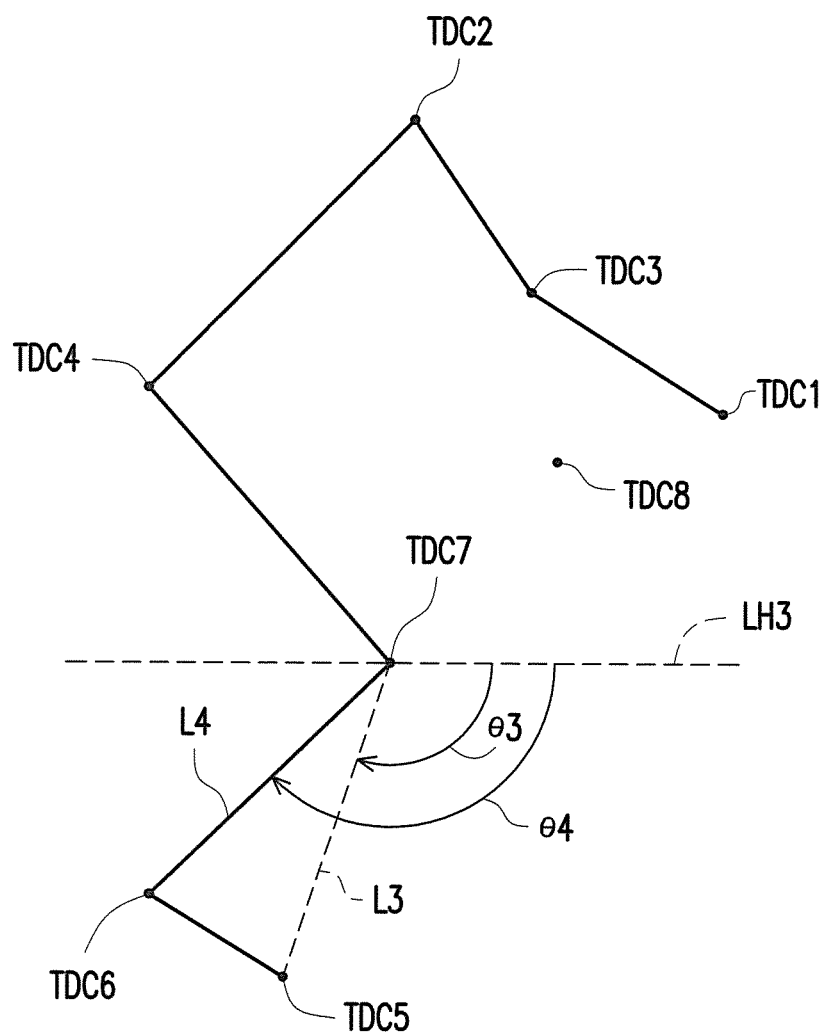
FIG. 5A and FIG. 5B are schematic diagrams illustrate the left emitting coordinates according to an embodiment of the invention.
Figure 5B:
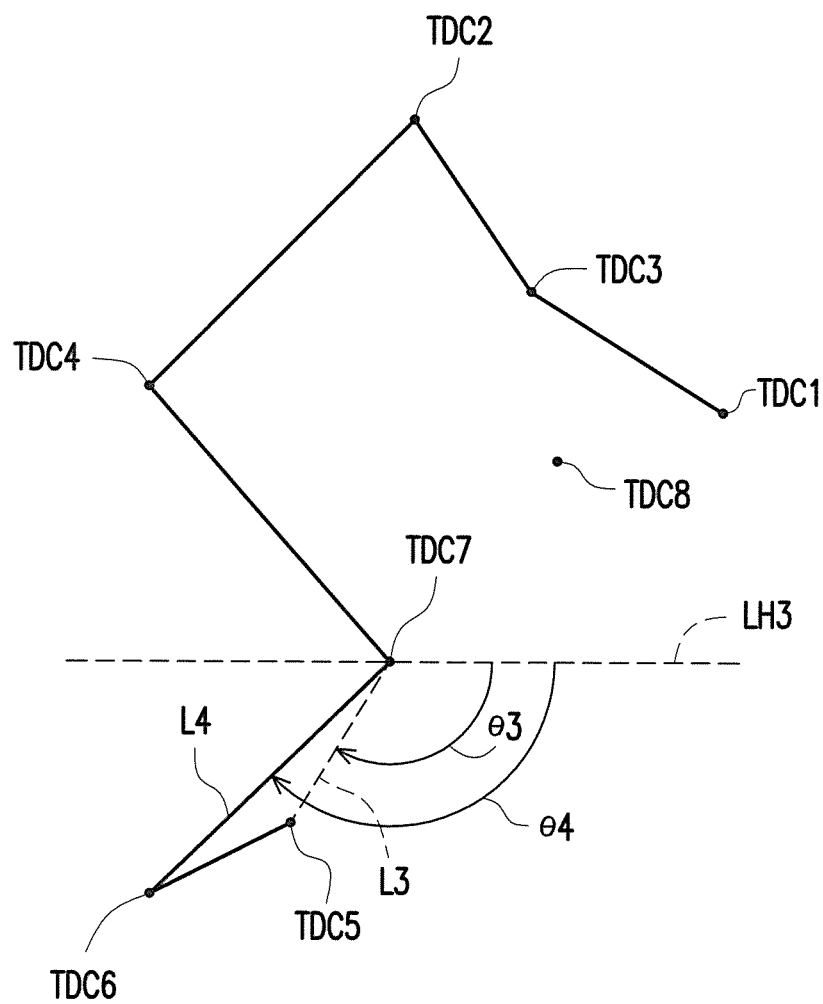

It should be mentioned that when the person to-be-tested rides the bicycle by raising the toes and pressing the heels, the emitting coordinate having the minimum coordinate value along the Y-axial direction is not the coordinate corresponding to the active independent emitting element on the toe. Accordingly, in an embodiment, the computer CP may determine whether the left emitting coordinate TDC5 having the minimum coordinate value along the Y-axial direction defined as the coordinate corresponding to the IR emitter 210_5 is correct according to the relative relationship among the left emitting coordinates TDC5 to TDC6. FIG. 5A and FIG. 5B are schematic diagrams illustrate the left emitting coordinates according to an embodiment of the invention. Furthermore, referring to FIG. 5A, the computer CP may further calculate a third included angle $\theta 3$ between a connection L3 between the coordinate corresponding to the IR emitter 210_7 and the coordinate corresponding to the IR emitter 210_5 and a horizontal line LH3 passing through the coordinate corresponding to the IR emitter 210_7, calculate a fourth included angle θ4 between a connection L4 between the coordinate corresponding to the IR emitter 210_7 and the coordinate corresponding to the IR emitter 210_6 and the horizontal line LH3, and compare whether a difference between the third included angle θ3 and the fourth included angle θ4 is within a present included angle range. The present included angle range may be determined based on actual requirements, and different present included angle ranges may be set according to bicycle types.

Referring to FIG. 5A, when the difference between the third included angle θ3 and the fourth included angle θ4 is within the present included angle range, the computer CP keeps the definition with respect to the coordinate corresponding to the IR emitter 210_6 and the coordinate corresponding to the IR emitter 210_5. In other words, the assumption that the computer CP defines that the left emitting coordinate TDC5 having the minimum coordinate value along the Y-axial direction as the coordinate corresponding to the IR emitter 210_5 in the beginning is correct.

On the other hand, referring to FIG. 5B, when the difference between the third included angle θ3 and the fourth included angle θ4 is not within the present included angle range, the computer CP modifies the definition with respect to the coordinate corresponding to the IR emitter 210_6 and the coordinate corresponding to the IR emitter 210_5. In other words, the assumption that the computer CP defines that the left emitting coordinate TDC6 having the minimum coordinate value along the Y-axial direction as the coordinate corresponding to the IR emitter 210_5 in the beginning is incorrect. Thus, the computer CP defines the left emitting coordinate TDC5 corresponding to the smaller third included angle θ3 as corresponding to the IR emitter 210_5 affixed to the toe and defines the left emitting coordinate TDC6 corresponding to the greater third included angle θ4 as corresponding to the IR emitter 210_6 affixed to the ankle.

It should be mentioned that if the person to-be-tested fix an active independent emitting element to an unexpected position, or the active independent emitting element is dropped during the testing process, the computing apparatus is incapable of correctly establishing the corresponding relationship between the emitting coordinate and each of the active independent emitting elements, which results in incapability of correctly detecting the dynamic motion of the person to-be-tested. Thus, the computing apparatus of the invention may first determine whether the emitting coordinates pass complete verification to avoid the generation of wrong analysis.

In the embodiment illustrated in FIG. 3, after defining the corresponding relationship between the left emitting coordinates TDC1 to TDC8 and the IR emitters 210_1 to 210_8, the computer CP may determine whether the left emitting coordinates TDC1 to TDC8 pass complete verification according to the corresponding relationship between the left emitting coordinates TDC1 to TDC8 and the IR emitters 210_1 to 210_8. Similarly, after defining the corresponding relationship between the right emitting coordinates TDC9 to TDC16 and the IR emitters 210_1 to 210_8, the computer CP may determine whether the right emitting coordinates TDC9 to TDC16 pass complete verification according to the corresponding relationship between the right emitting coordinates TDC9 to TDC16 and the IR emitters 210_1 to 210_8.

If the left emitting coordinates TDC1 to TDC8 pass the complete verification, and the right emitting coordinates TDC9 to TDC16 pass the complete verification, the computer CP calculates a plurality of 3D coordinates respectively corresponding to the IR emitters 210_1 to 210_8 according to the left emitting coordinates TDC1 to TDC8 and the right emitting coordinates TDC9 to TDC16, so as to construct the riding motion of the person to-be-tested TB.

For the left emitting coordinates TDC1 to TDC8, the aforementioned complete verification includes checking whether the number of the left emitting coordinates TDC1 to TDC8 is equal to a preset value, checking whether relative positions among the left emitting coordinates TDC1 to TDC8 are correct, or checking whether angles formed according to the left emitting coordinates TDC1 to TDC8 are within a preset range. Specifically, when any one of the IR emitters 210_1 to 210_8 is fixed to an unexpected position, the computer CP may further issue a warning to the person to-be-tested TB to prompt that the detecting left emitting coordinates TDC1 to TDC8 do not pass the complete verification.

Taking the examples illustrated in FIG. 2 and FIG. 3 for example, the computer CP has to determine whether the number of the left emitting coordinates on the left-eye image is equal to a preset value of '8' (i.e., the number of the IR emitters 210_1 to 201_8). Additionally, the computer CP has to determine whether a distance between the left emitting coordinate TDC2 having the maximum coordinate value along the Y-axial direction and the left emitting coordinate TDC3 having the minimum coordinate value along the Y-axial direction is greater than a preset distance, thereby determining whether the relative position between two left emitting coordinates is correct. On the other hand, after defining the corresponding relationship between each of the left emitting coordinates TDC1 to TDC8 and the IR emitters 210_1 to 210_8, the computer CP may generate a plurality of connections connected with the coordinates respectively corresponding to the IR emitters 210_1 to 210_8 according to the corresponding relationship and check whether the angles among the connections are within a preset range.

It should be mentioned that the description above is made by illustrating the computer CP as operating according to the 2D left emitting coordinates TDC1 to TDC8 and the 2D right emitting coordinates TDC9 to TDC16 for example, but the invention is not limited thereto. In another embodiment, the two-eye image capturing apparatus 220 may first generate the corresponding 3D coordinates according to the left emitting coordinates on the left-eye image and the right emitting coordinates on the right-eye image and then, may define the corresponding relationship between each 3D coordinate and the IR emitters 210_1 to 210_8 according to the geometry relationship among the 3D coordinates. Similarly, the computer CP may also determine whether the 3D coordinates obtained through calculation pass the complete verification.

It should be noted here that the invention is not intent to limit the sequence of determining each of the emitting coordinates TDC1 to TDC8. In other embodiments, geometry positions of the wrist, the elbow, the waist, the shoulder, the toe, the ankle and the knee may be determined simultaneously or in a sequence different from the aforementioned sequence, but the invention is not limited thereto.

It should be additionally noted that the geometry relationship determination is only described as an example and construes no limitation to the invention to identify the corresponding relationship between the emitting coordinates and the marked points only through the geometry relationship determination. For example, in the case of determining the emitting coordinate corresponding to the IR emitter 210_4 on the waist, the determination is performed based on the coordinate values along the X-axial direction; however, in other embodiments, the computer CP may also determine which coordinate is corresponding to the marked point on the waist by comparing an angle relationship between each undefined emitting coordinate and the shoulder and an angle relationship between each undefined emitting coordinate and the ankle after the emitting coordinates corresponding to the shoulder and the ankle are obtained. In other words, any system that defines the corresponding relationship between the emitting coordinates TDC1 to TDC8 and IR emitters 210_1 to 210_8 by determining the geometry relationship among the emitting coordinates TDC1 to TDC8 in the same image frame falls within the scope to be protected by the invention.

In light of the foregoing, the invention provides a dynamic motion detection system marking the body parts of the person to-be-tested by using the active independent emitting elements. The positioning signal of each marked point is an independently emitted signal and is actively emitted, rather than passively detected, and thus, the system of the invention can contribute to preventing the exercise motions of the person to-be-tested from being affected by the wire and reducing the environment interference, so as to enhance accuracy of detecting the marked points. Moreover, in the invention, the corresponding relationship between the detected 3D coordinates and the marked points is determined according to the relative geometry relationship among each of the marked points, and thereby, the exercise motion model of the person to-be-tested can be analyzed and established only according to the information in a signal image frame, so as to improve continuity and accuracy of the detected motions.

Although the invention has been disclosed by the above embodiments, they are not intended to limit the invention. It will be apparent to one of ordinary skill in the art that modifications and variations to the invention may be made without departing from the spirit and scope of the invention. Therefore, the scope of the invention will be defined by the appended claims.

What is claimed is:

1. A dynamic motion detection system, comprising:
   a plurality of active independent emitting elements, respectively affixed to different parts of a person to-be-tested, and each of the active independent emitting elements being configured to actively emit a positioning signal having a preset wavelength;
   a signal capturing apparatus, configured to capture the positioning signal of each of the active independent emitting elements and obtain a plurality of emitting coordinates according to the positioning signals; and
   a computing apparatus, configured to control operation of the signal capturing apparatus and receive the emitting coordinates from the signal capturing apparatus,
   wherein the computing apparatus defines a corresponding relationship between the emitting coordinates and the active independent emitting elements by comparing a geometry relationship among the emitting coordinates,
   wherein the signal capturing apparatus comprises:
   a first image capturing module, configured to capture a left-eye image;
   a second image capturing module, disposed at a position with a predetermined interval from the first image capturing module, and configured to capture a right-eye image; and
   an image processing module, coupled to the first image capturing module and the second image capturing module, and configured to calculate a plurality of left emitting coordinates of the left-eye image according to the positioning signals and calculate a plurality of right emitting coordinates of the right-eye image according to the positioning signals, wherein the emitting coordinates comprise the right emitting coordinates and the left emitting coordinates,
   wherein the computing apparatus defines a corresponding relationship between the left emitting coordinates and the active independent emitting elements by comparing a geometry relationship among the left emitting coordinates,
   wherein the computing apparatus determines whether the left emitting coordinates pass a complete verification according to the corresponding relationship between the left emitting coordinates and the active independent emitting elements.

2. The dynamic motion detection system according to claim 1, wherein when a dynamic motion of the person to-be-tested is detected, the active independent emitting elements are controlled to simultaneously emit the positioning signals.

3. The dynamic motion detection system according to claim 1, wherein each of the active independent emitting elements is a light-emitting diode (LED).

4. The dynamic motion detection system according to claim 1, wherein the preset wavelengths of the positioning signals ranges from 760 nm to 1000 nm.

5. The dynamic motion detection system according to claim 4, wherein each of the active independent emitting elements is an infrared (IR) emitter.

6. The dynamic motion detection system according to claim 1, wherein each of the active independent emitting elements is an active radio frequency identification (RFID) tag.

7. The dynamic motion detection system according to claim 1, wherein the signal capturing apparatus further comprises:
   a filter module, disposed on the first image capturing module and the second image capturing module, and configured to filter signals having wavelengths other than the preset wavelength.

8. The dynamic motion detection system according to claim 1, wherein the complete verification comprises whether the number of the left emitting coordinates is equal to a preset value, whether relative positions among the left emitting coordinates are correct, or whether angles formed according to the left emitting coordinates are within a preset range.

9. The dynamic motion detection system according to claim 1, wherein when the left emitting coordinates pass the complete verification, and the right emitting coordinates pass the complete verification, the computing apparatus calculates a plurality of 3D coordinates respectively corresponding to the active independent emitting elements according to the left emitting coordinates and the right emitting coordinates.

10. The dynamic motion detection system according to claim 1, wherein the computing apparatus analyzes a change of the 3D coordinate corresponding to each of the active independent emitting elements during a detection period, so as to generate a dynamic motion detection result.

11. The dynamic motion detection system according to claim 10, further comprising:
   a display apparatus, coupled to the computing apparatus and configured to display the dynamic motion detection result.

12. The dynamic motion detection system according to claim 1, wherein the dynamic motion detection system is configured to detect a bicycle riding motion of the person to-be-tested, and the parts comprises at least one of a wrist, a shoulder, an elbow, a buttock, an ankle, a toe and a knee, wherein the emitting coordinates are defined based on a first axial direction and a second axial direction, and the first axial direction and the second axial direction are not parallel to each other.

13. The dynamic motion detection system according to claim 12, wherein the computing apparatus defines one of the emitting coordinates having a maximum coordinate along the first axial direction as a coordinate corresponding to a first active independent emitting element affixed to the shoulder.

14. The dynamic motion detection system according to claim 12, wherein the computing apparatus defines one of the emitting coordinates having a maximum coordinate along the second axial direction as a coordinate corresponding to a second active independent emitting element affixed to the wrist.

15. The dynamic motion detection system according to claim 14, wherein the computing apparatus defines one of the emitting coordinates having a maximum coordinate along the first axial direction as the coordinate corresponding to the first active independent emitting element affixed to the shoulder,
wherein the computing apparatus defines one of the undefined emitting coordinates between the coordinate corresponding to the first active independent emitting element and the coordinate corresponding to the second active independent emitting element as a coordinate corresponding to a third active independent emitting element affixed to the elbow.

16. The dynamic motion detection system according to claim 12, wherein the computing apparatus defines one of the undefined emitting coordinates having no displacement as a coordinate corresponding to one of the active independent emitting elements affixed to a reference point.

17. The dynamic motion detection system according to claim 12, wherein the computing apparatus defines one of the emitting coordinates having a minimum coordinate along the second axial direction as a coordinate corresponding to a fourth active independent emitting element affixed to the buttock.

18. The dynamic motion detection system according to claim 17, wherein the computing apparatus respectively connects the undefined emitting coordinates with the coordinate corresponding to the fourth active independent emitting element respectively to obtain a plurality of second connections,
wherein the computing apparatus determines a plurality of second included angles between the second connections and a horizontal line passing through the coordinate corresponding to the fourth active independent emitting element,
wherein the computing apparatus defines one of the undefined emitting coordinates corresponding to a minimum second included angle as a coordinate corresponding to a fifth active independent emitting element affixed to the knee.

19. The dynamic motion detection system according to claim 18, wherein the computing apparatus defines one of the undefined emitting coordinates having a minimum coordinate along the first axial direction as a coordinate corresponding to a sixth active independent emitting element affixed to the toe, and defines one of the emitting coordinates closest to the coordinate corresponding to the sixth active independent emitting element as a coordinate corresponding to a seventh active independent emitting element affixed to the ankle.

20. The dynamic motion detection system according to claim 19, wherein the computing apparatus further calculates a third included angle between a connection between the coordinate corresponding to the sixth active independent emitting element and the coordinate corresponding to the fifth active independent emitting element and a horizontal line passing through the coordinate corresponding to the fifth active independent emitting element, calculates a fourth included angle between a connection between the coordinate corresponding to the seventh active independent emitting element and the coordinate corresponding to the fifth active independent emitting element and the horizontal line passing through the coordinate corresponding to the fifth active independent emitting element, and compares whether a difference between the third included angle and the fourth included angle is within a present included angle range,
wherein if the difference between the third included angle and the fourth included angle is within the present included angle range, the computing apparatus keeps the definition with respect to the coordinate corresponding to the six and the seventh active independent emitting elements, and
if the difference between the third included angle and the fourth included angle is not within the present included angle range, the computing apparatus modifies the definition with respect to the coordinate corresponding to the six and the seventh active independent emitting elements.

* * * * *